US006203845B1

(12) United States Patent
Qin et al.

(10) Patent No.: US 6,203,845 B1
(45) Date of Patent: Mar. 20, 2001

(54) DEHYDRATED HYDROGELS

(75) Inventors: Yimin Qin, Northwich; Keith Dennis Gilding, Winsford, both of (GB)

(73) Assignee: Advanced Medical Solutions Limited, Winsford Cheshire (GB)

( * ) Notice: Subject to any disclaimer, the term of this patent is extended or adjusted under 35 U.S.C. 154(b) by 0 days.

(21) Appl. No.: 09/171,302

(22) PCT Filed: Apr. 21, 1997

(86) PCT No.: PCT/GB97/01098

§ 371 Date: Jul. 26, 1999

§ 102(e) Date: Jul. 26, 1999

(87) PCT Pub. No.: WO97/39781

PCT Pub. Date: Oct. 30, 1997

(30) Foreign Application Priority Data

Apr. 20, 1996 (GB) .................................... 96082227

(51) Int. Cl.⁷ ...................... A61L 15/00; A61F 13/00; C08J 5/04; C12N 11/10
(52) U.S. Cl. ...................... 427/2.31; 424/443; 521/66; 435/178
(58) Field of Search ...................... 427/2.31; 424/443; 536/128; 521/66; 435/178

(56) References Cited

U.S. PATENT DOCUMENTS

| 5,409,703 | * | 4/1995 | McAnalley et al. | 424/435 |
| 5,541,234 | * | 7/1996 | Unger et al. | 521/66 |
| 5,648,252 | * | 7/1997 | Dumitriu et al. | 435/179 |
| 5,820,918 | * | 10/1998 | Ronan et al. | 427/2.1 |

FOREIGN PATENT DOCUMENTS

| 0613693A1 | * | 7/1994 | (EP) | A61L/15/28 |
| 96/13285 | * | 7/1994 | (WO) | A61L/25/00 |

OTHER PUBLICATIONS

Hawley, George G. The Condensed Chemical Dictionary 10th ed., pp. 502 and 865, 1981.*

* cited by examiner

Primary Examiner—Shrive Beck
Assistant Examiner—Jennifer Kolb
(74) Attorney, Agent, or Firm—Woodard, Emhardt, Naughton, Moriarty & McNett; Clifford W. Browning

(57) ABSTRACT

A method of producing a dehydrated hydrogel comprises dispensing fibers into an aqueous solution of a hydrogel precursor material incorporating a plasticiser, the fibers incorporating cations which are capable of cross-linking said precursor material to form a hydrogel, and freeze drying the mixture thus produced to provide a dehydrated hydrogel which incorporates said fibers, the dehydrated hydrogel being cross-linked by said cations.

10 Claims, No Drawings

DEHYDRATED HYDROGELS

The present invention relates to dehydrated hydrogels which are useful in the treatment of wounds.

A hydrogel is a cross-linked macromolecular network swollen with water or biological fluids. A dehydrated hydrogel is a cross-linked macro-molecular network that will swell to form a hydrogel upon contact with water or biological fluids. Due to their 'dehydrated' condition, dehydrated hydrogels are easy to store and transport. In addition, when applied in the dry state to a wound they behave as superabsorbent materials.

Our co-pending PCT Application No. PCT/GB95/02543 (WO-A-96/13285) discloses a method of producing a dehydrated hydrogel comprising dispersing fibres into an aqueous solution of a hydrogel precursor material incorporating a plasticiser, the fibres incorporating cations which are capable of cross-linking said precursor material to form a hydrogel, and evaporating water to produce a dehydrated hydrogel which incorporates said fibres, the dehydrated hydrogel being cross-linked by said cations.

According to the present invention there is provided a method of producing a dehydrated hydrogel comprising dispersing fibres into an aqueous solution of a hydrogel precursor material incorporating a plasticiser, the fibres incorporating cations which are capable of cross-linking said precursor material to form a hydrogel, and freeze drying the mixture thus produced to provide a dehydrated hydrogel which incorporates said fibres, the dehydrated hydrogel being cross-linked by said cations.

Therefore in the method of the invention water is evaporated from the admixture of hydrogel precursor material, fibres and plasticiser by a freeze drying procedure. Known conditions for freeze drying may be employed. Thus, for example, the admixture may be frozen below $-10°$ C. to form a solid product (e.g. a sheet) in which the hydrogel precursor is embedded in ice. The frozen mixture may then be subjected to a high vacuum so as to allow conversion of water from solid ice to water vapour (without passing through an intermediate liquid phase). The freeze drying procedure may be carried out using an Edwards freeze drying machine.

As a result of the method of the invention, the delicate pore structure of the frozen mixture is preserved and the final product (dehydrated hydrogel) is porous and highly absorbent.

The dehydrated hydrogel produced by the method of the invention may be in the form of a film having a thickness of, for example, 20 microns to 10 mm.

The dehydrated hydrogels produced by the method of the invention have a number of advantages. In particular, the presence of the fibres imparts strength and dimensional stability to the dehydrated hydrogel. Furthermore films of the dehydrated hydrogels have the property of swelling in only the thickness dimensions and not in the other two dimensions (as compared to films of conventional dehydrated hydrogels which swell in all three dimensions).

Typically, the dehydrated hydrogels will comprise (based on the total weight of the fibres, polymer forming the hydrogel, and plasticiser, i.e. excluding water and other components) 15 to 40% by weight of fibres, 10 to 35%, and 5 to 75% plasticiser. More preferably the fibres and polymer together provide about 40–60% ideally about 50% by weight on the same weight basis so that correspondingly the plasticiser provides 60–40%, ideally about 50%. Generally the amount of fibres will exceed the amount of polymer. For example the weight ratio may be 1.5–3:1. Typically the dehydrated hydrogel will contain less than 50% by weight of water, ideally less than 20%, based on the total weight of the dehydrated hydrogel.

Examples of hydrogel precursor material which may be used include sodium alginate, sodium carboxymethyl cellulose, sodium pectinate, sodium O-carboxymethyl chitosan (OCC), sodium N,O-carboxymethyl chitosan (NOCC), sodium polyacrylate, and naturally occurring gums and synthetic polymers containing pendant carboxylic acid groups (hummectants).

The hydrogel precursor may consist wholly or partially of Ace Mannan (or other component of Alloe Vera) which is a natural polymer known to accelerate healing of wounds. The Ace Mannan may, for example, provide up to 80% of the matrix. The Ace Mannan may be clinical grade material obtainable from Carrington Laboratories, Dallas, Tex., USA.

The fibres which are used contain a di- or higher valent cation which is effective for cross-linking the hydrogel. Examples of suitable cations include $Ca^{2°}$, $Zn^{2+}$, and cations which also act as enzyme cofactors. Particular preferred examples of fibres which may be used are calcium alginate fibres. The fibres will generally have a length of 1 to 80 mm and a thickness of 10 to 50 microns.

The fibres may be such that they absorb water from the aqueous solution of the hydrogel precursor material during manufacture of the dehydrated hydrogel.

Examples of suitable plasticisers include glycerol, polyethylene glycol, sorbitol and similar sugars, and pluronic type PEO/PPO polymers.

In a typical method of preparing a dehydrated hydrogel in accordance with the invention, the fibres, polymer and plasticiser in their relative requisite amounts are admixed with water such that the fibres, polymer and plasticiser together provide less than 5% by weight (e.g. less than 3%, e.g. 2%) of the resultant mixture. After thorough mixing, the dispersion may be cast to an appropriate thickness and freeze dried to give a dehydrated hydrogel product containing less than 50% water, more usually 20% or less.

Dehydrated hydrogels have a number of advantages. In particular when applied to the wounds (e.g. donor sites, abrasions, dermabrasions, surface wounds with high exudate or wide savings in exudate levels) they are capable of absorbing large amounts of exudate, e.g. up to 30 times their own weight, thereby rehydrating to form a hydrogel. If the dehydrated hydrogel is in the form of a film, it is found that the film swells in the thickness dimension without substantial swelling in the other two dimensions. Upon sufficient absorption of exudate, the film is capable of dissolving. The product of the invention is more absorbent than current commercial hydrogels, and is also light and easy to package.

Dehydrated hydrogels produced in accordance with the method of this invention may be laminated to hydrophilic films which have an increased breathability in the presence of liquid water as compared to moisture vapour alone. The use of such a film over the dehydrated hydrogel (i.e. on the side remote from the wound) ensures that water is vented from the dehydrated hydrogel through the film. Therefore the dissolution of the hydrogel may be controlled.

Typically the breathable film will be of a material which, as a 50 micron film, has an MVTR in the presence of moisture vapour alone of 6,000 to 10,000 g m$^{-2}$ 24 hr$^{-1}$ as measured by ASTM E96B and an MVTR in the presence of liquid water (as measured by ASTM E96BW) of 6,000 to 10,000 g m$^{-2}$ 24 hr$^{-1}$. Typically the breathable film will have a thickness of 30–70 microns, more preferably 40–60 microns, e.g. about 50 microns.

The breathable film may for example be of polyurethane. Suitable films are available from Innovative Technologies Limited under the designations IT325, IT425 and IT625.

If desired, the dehydrated hydrogel may incorporate an active agent (e.g. an antimicrobial material) for delivery to a wound.

The invention will be further described by the following non-limiting Examples.

EXAMPLE 1

3 Grams of MF1-2B fibres (calcium alginate fibres available from Innovative Technologies) were cut to about 10 mm length. The fibres were mixed with 2 g of sodium alginate powder (protonol LF10/6OLS, ex Pronova), 5 g of glycerol and 1000 ml of water. The mixture was then placed into a stainless steel dish (23 cm×23 cm) to form a gel pre-cursor solution. The solution was then placed in a freezer (T<−10° C.) so that the gel pre-cursor frozen to form a solid ice. The dish was then taken immediately to a freeze frying machine (Edwards) to prepare the freeze dried pad and dried over a period of about 20 hours.

The resultant product was a dehydrated hydrogel capable of absorbing at least 20 grams of normal saline for a 10 cm×10 cm pad.

EXAMPLE 2

3Grams of MF1-21B fibres (calcium/sodium alginate fibres available from Innovative Technologies) were cut to about 50 mm length. The fibres were mixed with 3 g of sodium alginate powder (Protonol LF10/60, ex Pronova), 6 g of glycerol and 1000 ml of water. The mixture was then placed into a stainless steel dish (23 cm×23 cm) to form a gel pre-cursor solution. The solution was then placed in a freezer (T<−10° C.) so that the gel pre-cursor frozen to form a solid ice. The dish was taken immediately to a freeze drying machine (Edwards) to prepare the freeze dried pad and dried over a period of about 20 hours.

The resultant product was a dehydrated hydrogel capable of absorbing at least 20 grams of normal saline for a 10 cm×10 cm pad.

What is claimed is:

1. A method of producing a dehydrated hydrogel comprising dispersing fibres into an aqueous solution of a hydrogel precursor material incorporating a plasticiser, the fibres incorporating cations which are capable of cross-linking said precursor material to form a hydrogel, and freeze drying the mixture thus produced to provide a dehydrated hydrogel which incorporates said fibres, the dehydrated hydrogel being cross-linked by said cations.

2. A method as claimed in claim 1 wherein the hydrogel precursor material is selected from sodium alginate, sodium carboxymethyl cellulose, sodium pectinate, sodium O-carboxymethyl chitosan (OCC), sodium N,O-carboxymethyl chitosan (NOCC), sodium polyacrylate, and naturally occurring gums and synthetic polymers containing pendant carboxylic acid groups (hummectants).

3. A method as claimed in claim 1 wherein the fibres contain $Ca^{2+}$, $Zn^{2+}$ and/or cations which also act as enzyme cofactors.

4. A method as claimed in claim 1 wherein the fibres are calcium alginate fibres.

5. A method as claimed in claim 2 wherein the hydrogel precursor material is sodium alginate.

6. A method as claimed in claim 5 wherein the fibres are calcium alginate fibres.

7. A method as claimed in claim 1 wherein the dehydrated hydrogel comprises 15 to 40% by weight of fibres, 10 to 35% by weight of polymer forming the hydrogel and 5 to 75% by weight of plasticiser, the percentages being based on the total weight of the fibres, polymer forming the hydrogel, and the plasticiser.

8. A method as claimed in claim 1 wherein the ratio by weight of the fibres to that of the polymer is 1.5–3:1.

9. A method as claimed in claim 1 wherein the dehydrated hydrogel contain less the 20% by weight of water based on the total weight of the dehydrated hydrogel.

10. A method as claimed in claim 1 wherein the fibres have a length of 1 to 80 mm and a thickness of 10 to 50 microns.

* * * * *

UNITED STATES PATENT AND TRADEMARK OFFICE
CERTIFICATE OF CORRECTION

PATENT NO.    : 6,203,845 B1
DATED         : March 20, 2001
INVENTOR(S)   : Yimin Qin and Denis Keith Gilding Page 1 of 1

It is certified that error appears in the above-identified patent and that said Letters Patent is hereby corrected as shown below:

Title page,
Please change the inventor's name from "Keith Dennis Gilding" to -- Denis Keith Gilding --.

Column 2,
Line 19, please change "$Ca^{2°}$" to -- $Ca^{2+}$ --.

Column 3,
Line 18, please change "frying" to -- drying --.

Column 4,
Line 33, please change "the" to -- than --.

Signed and Sealed this

Twenty-eighth Day of May, 2002

Attest:

JAMES E. ROGAN
*Attesting Officer*    *Director of the United States Patent and Trademark Office*